United States Patent
Oldani

(10) Patent No.: US 10,661,232 B2
(45) Date of Patent: May 26, 2020

(54) REACTION DEVICE WITH AIR-LIFT TYPE INTERNAL CIRCULATION

(71) Applicant: Eni S.p.A., Rome (IT)

(72) Inventor: Fabio Oldani, Parabiago (IT)

(73) Assignee: Eni S.P.A., Rome (IT)

( * ) Notice: Subject to any disclaimer, the term of this patent is extended or adjusted under 35 U.S.C. 154(b) by 0 days.

(21) Appl. No.: 15/525,645

(22) PCT Filed: Nov. 11, 2015

(86) PCT No.: PCT/EP2015/076337
§ 371 (c)(1),
(2) Date: May 10, 2017

(87) PCT Pub. No.: WO2016/075194
PCT Pub. Date: May 19, 2016

(65) Prior Publication Data
US 2017/0326507 A1    Nov. 16, 2017

(30) Foreign Application Priority Data

Nov. 12, 2014 (IT) .............. MI2014A1944

(51) Int. Cl.
*B01F 3/04* (2006.01)
*C12M 1/00* (2006.01)
(Continued)

(52) U.S. Cl.
CPC ......... *B01F 3/04517* (2013.01); *C12M 27/24* (2013.01); *C12M 29/08* (2013.01);
(Continued)

(58) Field of Classification Search
CPC ...... B01F 2215/0422; B01F 2215/0431; B01F 3/00; B01F 3/04517; C12M 1/00; C12M 27/24; C12M 29/08
(Continued)

(56) References Cited

U.S. PATENT DOCUMENTS 3,628,775 A    12/1971   McConnell et al.
3,953,003 A *   4/1976   Mahig ................. B01F 3/04517
                                                         366/101
(Continued)

FOREIGN PATENT DOCUMENTS

GB            1383432      *  2/1975
GB            2037174 A        7/1980
WO        WO9217409 A1       10/1992

OTHER PUBLICATIONS

International Search Report for PCT/EP2015/076337 dated Feb. 22, 2016, 3 pages.
(Continued)

*Primary Examiner* — Claire A Norris
(74) *Attorney, Agent, or Firm* — Praedcere Law

(57) ABSTRACT

The present invention relates to a reaction device with air-lift type internal circulation which includes: a vertical cylindrical volume (1), more than one draft tube vertical element (2) positioned within the cylindrical volume (1) in such a manner as to form an gap with the walls of said volume, more than one gas distributor (3), each of which is positioned on the bottom of said device; wherein: each vertical internal element (2) has an internal diameter which increases along the vertical axis of said element, and the ratio between the total height of the reaction device and the internal diameter of the reaction device is less than 1.

7 Claims, 5 Drawing Sheets

(51) Int. Cl.
*C12M 1/08* (2006.01)
*B01F 3/00* (2006.01)

(52) U.S. Cl.
CPC ......... *B01F 3/00* (2013.01); *B01F 2215/0422* (2013.01); *B01F 2215/0431* (2013.01); *C12M 1/00* (2013.01)

(58) Field of Classification Search
USPC ...................................................... 210/151
See application file for complete search history.

(56) References Cited

U.S. PATENT DOCUMENTS

| | | |
|---|---|---|
| 4,504,388 A | 3/1985 | Desbos et al. |
| 2003/0147791 A1 | 8/2003 | Ding et al. |

OTHER PUBLICATIONS

"Biochemical Engineering Fundamentals"; J.E. Bailey, D.F. Ollis; McGraw-Hill; second edition; 1986.
W. Jianping, J. Xiaoqiang, P. Lei, W. Changlin, M. Guozhu; "Nitrifying Treatment of Wastewater from Fertilizer Production in a Multiple Air Lift Loop Bioreactor"; Biochem. Eng. J.; 25; [2005].
P. Wongsuchoto, P. Pavasant; "Internal Liquid Circulation in Annulus Sparged Internal Loop Airlift Contactors"; Chem. Eng. J.; 100; [2004].
R. Krishna, M.I. Urseanu, J.M. van Baten, J. Ellenberger; "Liquid Phase Dispersion in Bubble Columns Operating in the Churn-Turbulent Flow Regime"; Chem. Eng. J.; 78; [2000].

* cited by examiner

REACTION DEVICE WITH AIR-LIFT TYPE INTERNAL CIRCULATION

The present invention relates to a reaction device with air-lift type internal circulation which may be used to carry out two-phase gas-liquid and three-phase gas-solid-liquid reactions.

In particular, said device may be used for carrying out fermentation reactions of aerobic microorganisms, such as for example yeasts.

In the present patent application, all the operating conditions mentioned in the text should be taken to be preferred conditions even if this is not explicitly stated.

For the purposes of the present explanations, the term "comprise" or "include" also encompasses the term "consist in" or "essentially consist of".

For the purposes of the present explanations, unless stated otherwise, range definitions always include the extremes.

Two-phase or three-phase reactors used for fermentation are typically bubble reactors or stirred reactors. Such reactors are somewhat inefficient and costly from an energy standpoint and application thereof is thus restricted by the scale and type of reaction.

Internal circulation reactors, commonly known as air-lift reactors, provide a tubular element, also known as a draft tube, within a bubble column, which element permits recirculation of the liquid phase, so improving mixing and mass transfer from the gas phase to the liquid phase ("*Biochemical Engineering Fundamentals*"; J. E. Bailey, D. F. Ollis; McGraw-Hill; second edition; 1986).

Conventional air-lift reactors, however, exhibit liquid recirculation, for example in the draft tube, which brings about a reduction in gas-phase holdup in the zone in which said recirculation proceeds.

Solutions adopted to reduce this phenomenon include multiple stage air-lift reactors which involve the introduction of multiple tubular elements (draft tubes) as described in W. Jianping, J. Xiaoqiang, P. Lei, W. Changlin, M. Guozhu; "*Nitrifying Treatment of Wastewater from Fertilizer Production in a Multiple Air Lift Loop Bioreactor*"; Biochem. Eng. J.; 25; [2005].

Patent application US 2003/0147791 relates to multiple draft tube air-lift internal circulation reactors used to carry out two-phase gas-liquid and multi-phase gas-liquid-solid reactions. Said patent application discloses a reactor which may internally contain more than one draft tube, which are arranged in parallel and configured in a plurality of stages in series. Each draft tube provides a gas distributor positioned on the bottom of the draft tube, internally or externally thereof. The described reactor is characterised by a ratio between the height of the reactor and the internal diameter thereof which ranges from 3 to 12, and a ratio between the diameter of the draft tube and the internal diameter of the reactor which ranges from 0.4 to 0.9. There may be from 1 to 6 draft tubes. The bottom of the draft tube is at a distance from the bottom of the reactor which ranges from 10 cm to 100 cm, while the top of the draft tube is at a distance of between 10 cm and 200 cm beneath the surface of the liquid phase.

The bioreactors may be bubble columns and in particular air-lift reactors. When used for industrial fermentation, they must have volumes of greater than 1000 $m^3$ due to the very long reaction times (of the order of days). The air-lift reactors permit, in comparison with bubble columns, greater homogeneity of the system due to the recirculation of liquid within them. Such recirculation is promoted by an increase in reactor height. However, when the ratio between the height and diameter of the reactor is greater than 10, disadvantages may arise from an economic standpoint due to higher costs for construction (greater quantities of materials) and energy (consumption associated with pumping air). Moreover, difficulties in distributing the gas in the riser tubes of air-lift reactors built on an industrial scale, where the internal diameter of the reactor may be as much as 6 m, are known (P. Wongsuchoto, P. Pavasant; "*Internal Liquid Circulation in Annulus Sparged Internal Loop Airlift Contactors*"; Chem. Eng. J.; 100; [2004]), due to liquid recirculation within the riser tube (R. Krishna, M. I. Urseanu, J. M. van Baten, J. Ellenberger; "*Liquid Phase Dispersion in Bubble Columns Operating in the Churn-Turbulent Flow Regime*"; Chem. Eng. J.; 78; [2000]).

The object of the present invention is accordingly that of improving the fluid-dynamic performance of air-lift type reaction devices having a ratio between the total height and internal diameter of the device of less than 1, in particular for those devices used industrially.

The Applicant has accordingly invented an air-lift type reaction device which contains more than one vertical internal element, also known as a draft tube, having a diameter which varies along the vertical axis of said element. Said device may be used for carrying out gas-liquid or gas-solid-liquid reactions and, thanks to specific geometric ratios, it makes possible to improve phase homogeneity and mass transfer.

Further purposes and advantages of the present invention will be more apparent from the following description and the appended figures, which are provided purely by way of non-limiting example.

All of FIGS. 1-5 are preferred embodiments according to the present invention.

DETAILED DESCRIPTION

The present invention provides a reaction device with air-lift type internal circulation which includes:
- a vertical cylindrical volume, which may preferably be a container or vessel,
- more than one vertical element, designated draft tube in the text, positioned within the cylindrical volume in such a manner as to form a gap with the walls of said volume,
- more than one gas distributor, each of which is positioned on the bottom of said device;

said device being characterised in that:
  each vertical internal element has an internal diameter which increases along the vertical axis thereof, and
  the ratio between the total height of the reaction device and the internal diameter of the reaction device is less than 1.

The vertical element inside the reaction device is preferably formed by three bodies, two cylindrical bodies having different diameters and a body in the form of a truncated cone, said bodies being connected to each other in such a manner that the minor base of the truncated cone coincides with one of the bases of the first cylindrical body and the major base of the truncated cone coincides with one of the bases of the second cylindrical body. The ratio between the height of the truncated cone in the draft tube and the height of the draft tube device itself preferably ranges from 0.03 to 0.25. As regards to the body in the form of a truncated cone, the angle formed by the intersection between the height extension of the truncated cone and the apothem extension preferably ranges from 15° to 30°.

Said geometry of the draft tubes allows the liquid to recirculate more quickly in the interior thereof, ensuring better mixing of the system.

The ratio between the cross-sectional area of the gap and the cross-sectional area of the vertical internal element preferably ranges from 1 to 3.

Preferably, the internal diameter of the reaction device must be from 1.5 to 5 times the internal diameter of the draft tubes.

The reaction device described here is more preferably characterised in that the ratio between the cross-sectional area of the gap and the cross-sectional area of the vertical internal element ranges from 1 to 3, and the ratio between the height and internal diameter of the reaction device is less than 1.

According to the present invention, a draft tube is an element positioned inside a reaction device which separates said device into two distinct zones by creating gap between the element, or elements if more than one is present, and the walls of the device itself. The draft tubes are vertical elements with a diameter which varies along the axis. In particular, taking as reference the lower base of the reaction device, the diameter of a draft tube is smaller in the vicinity of said base and increases along the vertical axis of the device with increasing distance from said base.

According to the present invention, a plurality of draft tubes may be arranged inside the reaction device according to a parallel configuration.

Figure 1:
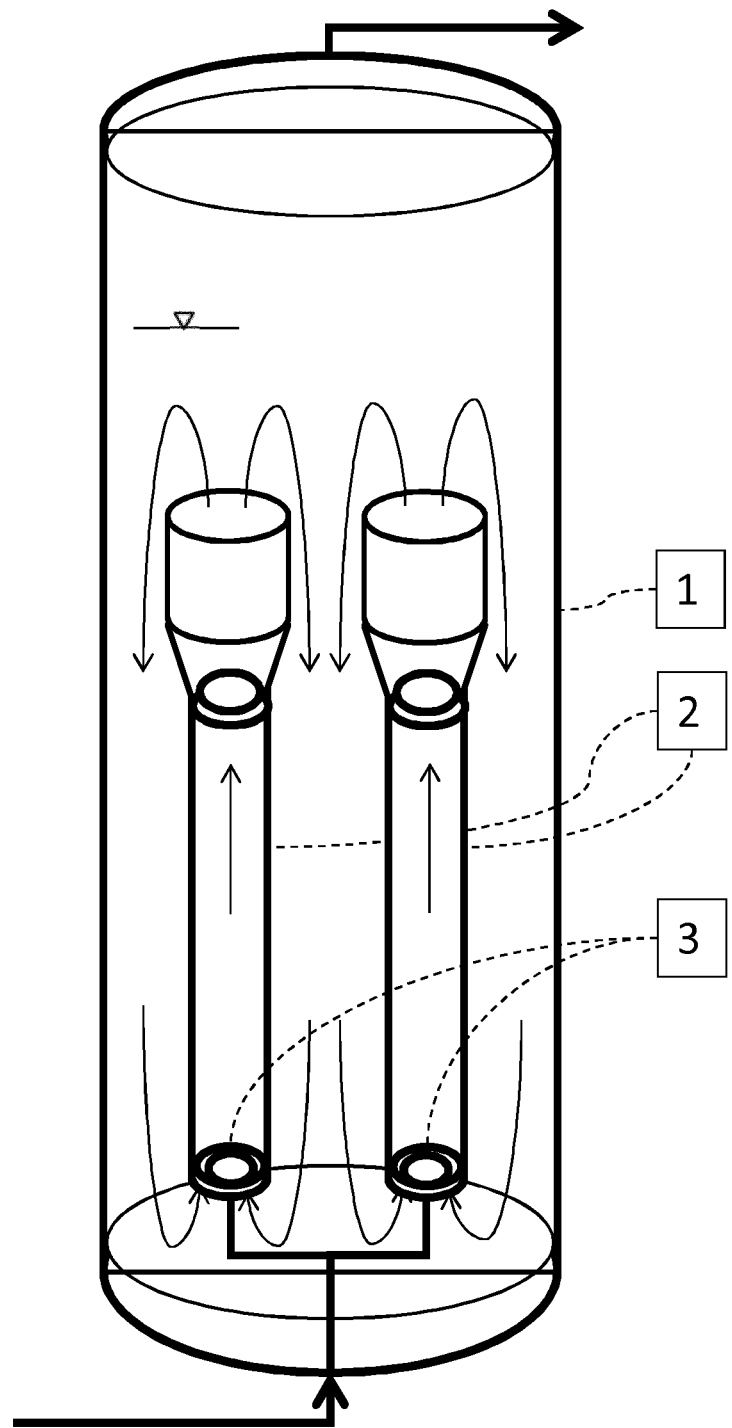
FIG. 1 is an air-lift type reaction device with two vertical elements or draft tubes, in which the draft tubes act as risers (2), and the volume of the reaction device functions as a downcomer (1). According to this configuration, the gas phase is distributed in each riser (2) through the distributors (3).

With reference to FIG. 1, during a gas-liquid or gas-solid-liquid reaction, a stream of gas introduced by way of appropriate distributors (3) into a reaction device (1), is segregated from the liquid or liquid-solid phase thanks to the internal draft tube element.

When the gas is fed in, zones of differing density are formed within the reaction device due to the presence of the draft tubes: a lower density zone where the gas is more concentrated and a higher zone where it is more dispersed. This difference in density activates the circulation of the liquid phase which tends to move upwards in the zone where the gas is more concentrated, said zone accordingly being designated riser, and in contrast to descend in the zone with a lower dispersed gas content, said zone accordingly being designated downcomer.

Figure 2:
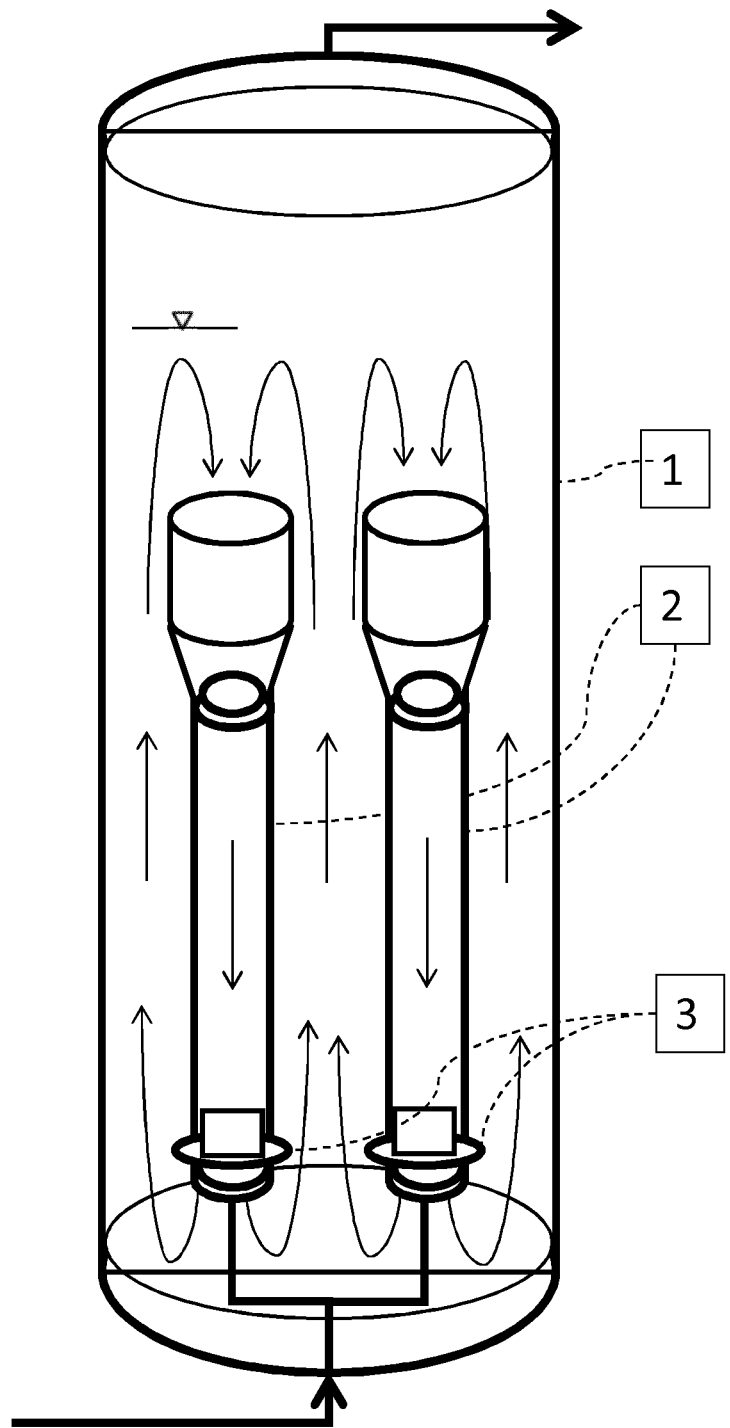
FIG. 2 is an air-lift type reaction device with two tubular draft tube elements, in which the draft tubes act as downcomers (2), and the volume of the reaction device functions as a riser (1). The gas phase is distributed in the riser (1) through the distributors (3).
Figure 3:
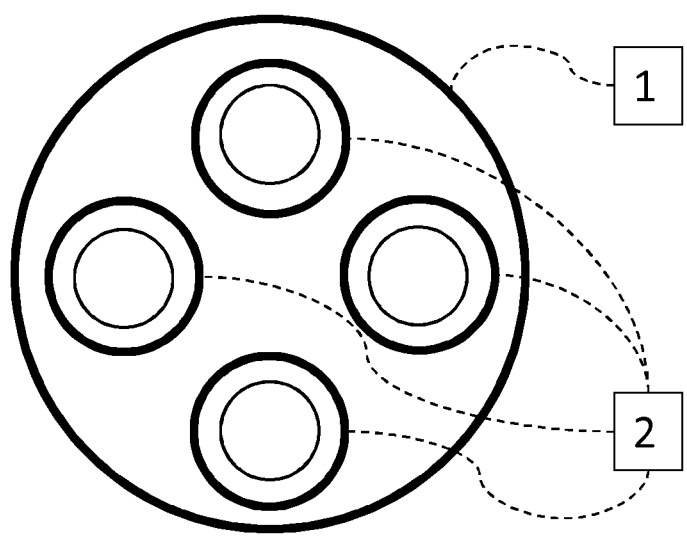
FIG. 3 is a section orthogonal to the axis of an air-lift type reaction device with four tubular draft tube elements.

The gas stream may also follow a different path, as shown in FIG. 2. In this case, the gas is distributed outside the draft tubes and the gap between the latter and the walls of the reaction device accordingly acts as a riser, while the "draft tube" acts as a downcomer.

The presence of a plurality of draft tubes inside the reaction device when the ratio between the area of the riser and the area of the downcomer ranges from 1 to 3, and when the ratio between the height and internal diameter of the reaction device is less than 1, results in greater gas phase holdup and greater recirculation velocity with a consequent increase in mass transfer.

The presence of a plurality of tubular draft tube elements inside the device makes it possible to obtain a homogeneous system even with ratios (total height of the reaction device)/(internal diameter of the reaction device) lower than 1. In this manner, it is possible to increase the volume of the reaction device, so improving the economic viability of the system (lower construction material costs and lower gas pumping costs for smaller column heights) without modifying the fluid-dynamic performances of the system.

Some illustrative, non-limiting examples of the present invention are provided below to assist in understanding the present invention and the implementation thereof.

Example 1 According to the Invention

Figure 4:
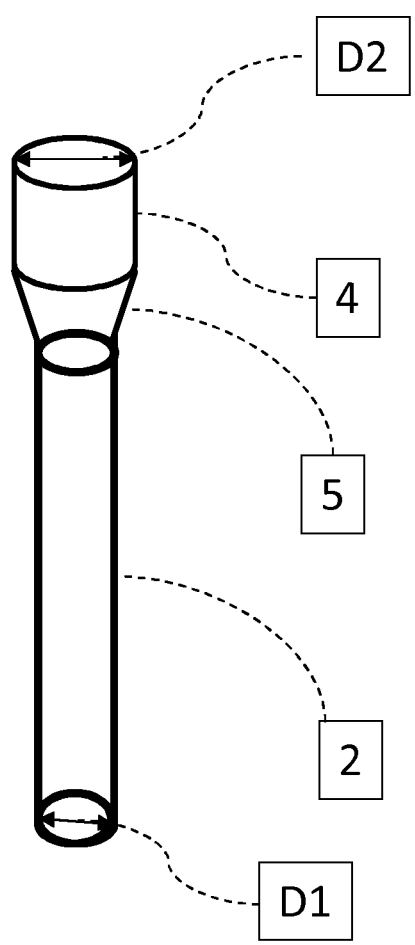
FIG. 4 shows a specific geometry of a draft tube with a variable diameter along the axis; said draft tube comprises three parts: a cylindrical part with diameter D1 (2), a truncated cone part with diameter D1<D2 (4) and a cylindrical part with diameter D2.
Figure 5:
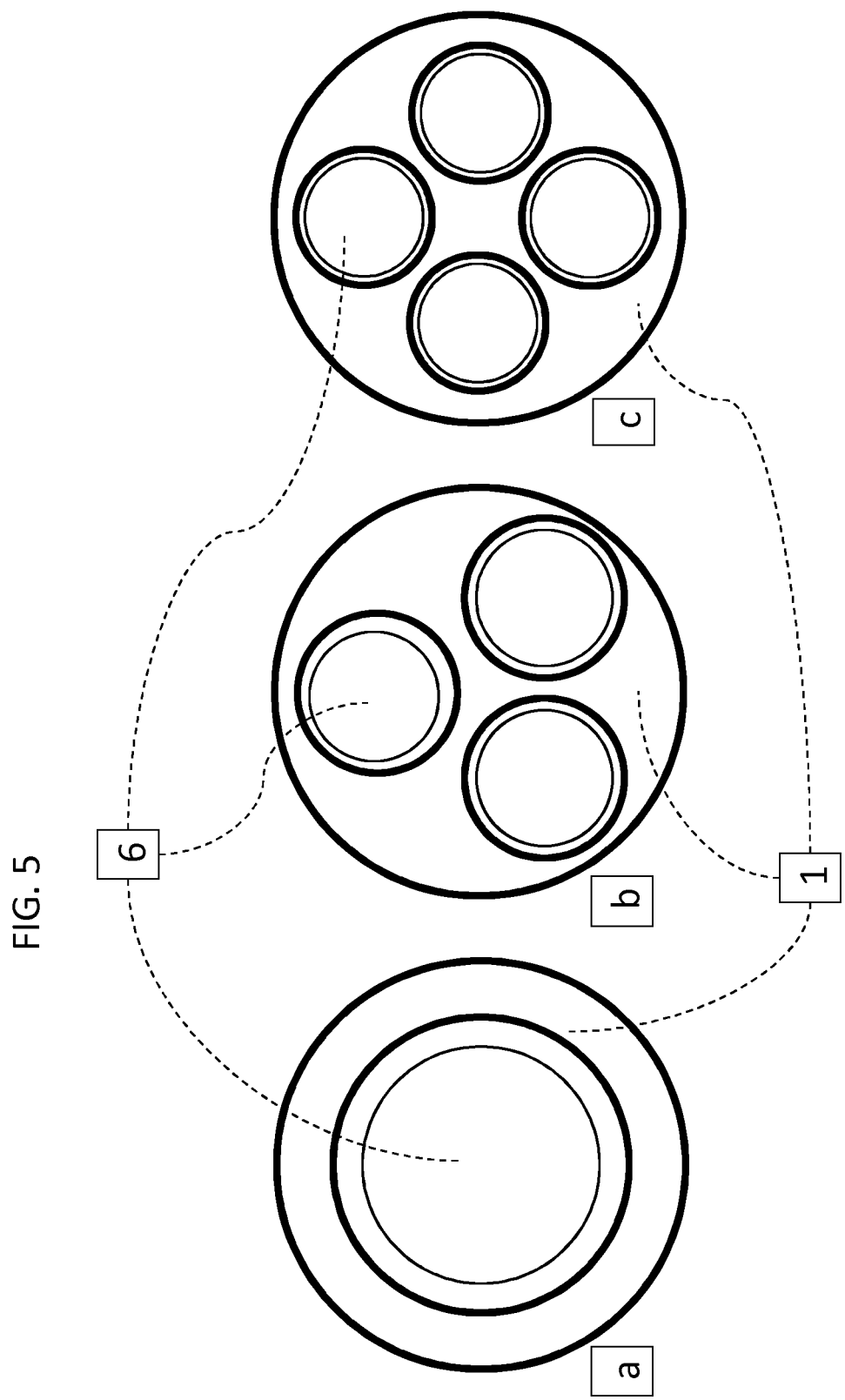
FIG. 5 shows some preferred configurations designated (a), (b) and (c) respectively having 1, 3 and 4 draft tubes (6).

With reference to FIG. 5, 20 $Nm^3/h$ of air were fed into an air-lift reactor of circular cross-section, with an internal diameter of 0.690 m and liquid depth of 0.470 m. From 1 to 4 draft tubes at a distance of 0.05 m from the bottom of the reactor were trialled. The air was fed into the individual draft tubes which thus act as risers (6), while the gap between the draft tubes and the reactor wall acts as a downcomer (1). The draft tubes are tubes with a variable cross-section with a total height of 0.350 m. Each draft tube is made up of a first cylindrical body, a truncated cone body of a height of 53 mm, with the angle formed by the intersection between the height extension of the truncated cone and the apothem extension being 20°, and the lower base coinciding with one of the bases of the first cylindrical body, and a second cylindrical body, the base of which coincides with the upper base of the truncated cone. With reference to the shape of the draft tubes shown in FIG. 4 and in the three configurations of FIG. 5, the table shows diameters of the draft tubes in the three different configurations.

TABLE

| FIG. 5 configuration | Number of draft tubes | Lower diameter, D1, FIG. 4 | Upper diameter, D2, FIG. 4 |
|---|---|---|---|
| a | 1 | 0.398 m | 0.437 m |
| b | 3 | 0.230 m | 0.269 m |
| c | 4 | 0.199 m | 0.238 m |

Three configurations respectively having 1, 3 and 4 draft tubes of a diameter such as to obtain a ratio between the cross-sectional area of the gap and the cross-sectional area of the internal elements of 2 in all three configurations were tested in the example. In these configurations, the oxygen mass transfer coefficient increases from 115.2 l/h with 1 draft tube to 208.8 l/h with 3 draft tubes and up to 266.4 l/h with 4 draft tubes.

Example 2 According to the Invention

Air was fed into an industrial aerobic fermentation reactor with an operating volume of 1000 $m^3$. Said reactor is made up of a cylindrical body with a diameter of 11.7 m and liquid depth of 9.3 m (total reactor height/internal reactor diameter ratio of 0.8). A single draft tube of a total height of 7.0 m and diameter at the base of 5.8 m is present inside the reactor. The "draft tube" has a geometry made up of a first cylindrical body with a diameter of 5.8 m, a truncated cone volume having a height of 1.1 m, an apothem (flare angle) of 20°, a lower base coincident with one of the surfaces of the first cylindrical body, and a second cylindrical body, the base of which coincides with the upper base of the truncated cone and has a diameter of 6.6 m. Said reactor was fed with 72 tons/h of air with an installed compressor power of 26.7 MW.

Comparative Example 1

An air-lift reactor of the same volume as that described in Example of the invention 2 used as an aerobic fermentation reactor containing a single draft tube of cylindrical geometry with constant cross-section and a diameter of 5.8 m, in which the total reactor height/internal reactor diameter ratio is equal to 3 was investigated. Said reactor was fed with 72 tons/h of air with an installed compressor power of 57.2 MW.

Furthermore, with identical operating volume, the reactor with a total reactor height/internal reactor diameter ratio of 0.8 described in Example of the invention 2, permits a 10% reduction in the material required for constructing the reactor body.

The invention claimed is:

1. A reaction device with air-lift type internal circulation, comprising:
    a vertical cylindrical volume;
    more than one vertical element positioned within the cylindrical volume in such a manner as to form a gap with the walls of said volume;
    more than one gas distributor, each of which is positioned on the bottom of said device;
    wherein each said vertical element has an internal diameter which increases along the vertical axis of said vertical element in an upward direction; and
    wherein the ratio between the total height of the reaction device and the internal diameter of the reaction device is less than 1,
    wherein each said vertical element is formed by three bodies, two cylindrical bodies having different diameters and a body in the form of a truncated cone, said bodies being connected to one another in such a manner that the minor base of the truncated cone coincides with the first cylindrical body and the major base of the truncated cone coincides with the second cylindrical body.

2. A device according to claim 1, in which the ratio between the height of the truncated cone and the height of the vertical element itself ranges from 0.03 to 0.25.

3. A device according to claim 1, in which, in relation to the body in the form of a truncated cone, the angle formed by the intersection between the height extension of the truncated cone and the apothem extension ranges from 15° to 30°.

4. A device according to claim 1, in which the ratio between the cross-sectional area of the gap and the cross-sectional area of said vertical element ranges from 1 to 3.

5. A device according to claim 1, in which the internal diameter of the reaction device is from 1.5 to 5 times the internal diameter of a single said vertical element.

6. A device according to claim 1, in which the ratio between the cross-sectional area of the gap and the cross-sectional area of said vertical element ranges from 1 to 3, and the ratio between the height and internal diameter of the reaction device is less than 1.

7. A device according to claim 1 wherein the walls of said vertical cylindrical volume have a constant diameter through the total height of said reaction device.

* * * * *